(12) United States Patent
Sekine et al.

(10) Patent No.: US 7,807,821 B1
(45) Date of Patent: Oct. 5, 2010

(54) METHOD FOR THE SYNTHESIS OF NUCLEIC ACID WITHOUT PROTECTING BASE MOIETY

(75) Inventors: Mitsuo Sekine, Yokohama (JP); Kohji Seio, Yokohama (JP); Akihiro Ohkubo, Machida (JP)

(73) Assignee: Japan Science and Technology Agency, Kawaguchi-shi (JP)

( * ) Notice: Subject to any disclaimer, the term of this patent is extended or adjusted under 35 U.S.C. 154(b) by 649 days.

(21) Appl. No.: 10/591,172

(22) PCT Filed: Feb. 24, 2005

(86) PCT No.: PCT/JP2005/003053

§ 371 (c)(1),
(2), (4) Date: Apr. 26, 2007

(87) PCT Pub. No.: WO2005/082923

PCT Pub. Date: Sep. 9, 2005

(30) Foreign Application Priority Data

Mar. 1, 2004 (JP) ............................. 2004-056707

(51) Int. Cl.
*C07H 21/00* (2006.01)
(52) U.S. Cl. .................. 536/25.31; 536/25.34
(58) Field of Classification Search ............... None
See application file for complete search history.

(56) References Cited

U.S. PATENT DOCUMENTS

2001/0008765 A1  7/2001  Shinoki et al.
2003/0096257 A1  5/2003  Shinoki et al.

FOREIGN PATENT DOCUMENTS

| JP | 62-51695 A | 3/1987 |
| JP | 11-80185 A | 3/1999 |
| JP | 2003-2895 A | 1/2003 |
| JP | 2003-28871 A | 1/2003 |
| JP | 2004-99532 A | 4/2004 |

OTHER PUBLICATIONS

Akihiro Ohkubo et al.; Tetrahedron Letters, 2004, vol. 45,, No. 2, pp. 363-366.
Wojciech Dabkowski et al.; Tetrahedron Letters, 2000, vol. 41, No. 39, pp. 7535-7539.
Takeshi Wada et al.; J. Am. Soc., 1997, No. 119, pp. 12710-12721.
Sergei M. Gryaznov et al.; Synthesis of Oligonucleotides via Monomers with Unprotected Bases, J. Am. Chem. Soc., 1991, No. 113, pp. 5876-5877.
Ohkubo et al., "A New Approach for Pyrophosphate Bond Formation Starting from Phosphoramidite Derivatives by Use Of 6-Trifluoromethyl-1-Hydroxybenzotriazole-Mediated O-N Phosphoryl Migration"; Tetrahedron Letters, Elsevier, Amsterdam, vol. 45, No. 5 , Jan. 26, 2004, pp. 979-982.
Seio K. et al., "Enhanced Stereoselectivity in Internucleotidic Bond Formation by the Use of The Chiral Ribose Moiety of Thymidine", Journal of Organic Chemistry, American Chemical Society, vol. 68, Jan. 1, 2003, pp. 3849-3859.
M. Sekine et al., "Proton-Block Strategy for the Synthesis of Oligodeoxynucleotides Without Base Protection, Capping Reaction, and P-N Bond Cleavage Reaction", Journal of Organic Chemistry, American Chemical Society, vol. 68, No. 14, 2003, pp. 5478-5492.
Ohkubo et al., "A New Strategy for the Synthesis of Oligodeoxynucleotides in the Phosphoramidite Method Without Base Protection Via Phosphite Intermediates", Nucleic Acid Research Supplement, vol. 2, 2002, pp. 29-30.

*Primary Examiner*—Lawrence E Crane
(74) *Attorney, Agent, or Firm*—Birch, Stewart, Kolasch & Birch, LLP.

(57) ABSTRACT

A phosphoramidite method for the synthesis of a nucleic acid oligomer without protecting the base moiety characterized in that a 3' or 5' hydroxyl group of a nucleotide is reacted with a nucleoside phosphoramidite, a cyclonucleoside phosphoramidite, a 2'-substituted nucleoside phosphoramidite, a 4'-substituted nucleoside phosphoramidite, or a 2',4'-di-substituted nucleoside phosphoramidite to produce a phosphodiester linkage. The phosphoramidite is contacted with an activator containing both a) hydroxybenzotriazole-1-ol (HOBt), a mono-substituted HOBt, a di-substituted HOBt, or a di-substituted phenol and b) imidazole, tetrazole, benzimidazoletriflate (BIT), 4-ethylthiotetrazole, imidazolium triflate(trifluoromethane sulfonate) or 4,5-dicyanoimidazole.

8 Claims, No Drawings

SEQUENCE LISTING

<160> NUMBER OF SEQ ID NOS: 2

<210> SEQ ID NO 1
<211> LENGTH: 19
<212> TYPE: DNA
<213> ORGANISM: Artificial Sequence
<220> FEATURE:
<223> OTHER INFORMATION: synthesized oligomer

<400> SEQUENCE: 1
cccccttttc tctctctct                    19

<210> SEQ ID NO 2
<211> LENGTH: 20
<212> TYPE: DNA
<213> ORGANISM: Artificial Sequence
<220> FEATURE:
<223> OTHER INFORMATION: synthesized oligomer

<400> SEQUENCE: 2
ttaaaaatta ttaaattatt                    20

METHOD FOR THE SYNTHESIS OF NUCLEIC ACID WITHOUT PROTECTING BASE MOIETY

This application claims priority to PCT/JP2005/0030503 filed on Feb. 24, 2004, under 35 U.S.C. § 120, and Japanese patent application 2004-056707, filed Mar. 1, 2004 under 35 U.S.C. § 119, the contents of both are herein incorporated by reference.

FIELD OF THE INVENTION

The invention relates to a method for the synthesis of a nucleic acid without protecting a base moiety, especially to a phosphoramidite method for the synthesis of a nucleic acid oligomer using an alcohol-type compound as an activator.

BACKGROUND ART

H-phosphonate method wherein hydroxyl group-selective condensation is carried out by means of a phosphonium-type condensing agent, BOMP, has been known for the method of synthesizing DNA without protecting a base moiety (Non-Patent Document 1). This reaction utilizes the phenomenon that an active phosphite intermediate generated during the condensation reaction will react more preferentially with a hydroxyl group than with an amino group in the base moiety.

[Non-Patent Document 1] Wada, T.; Sato, Y.; Honda, F.; Kawahara, S.; Sekine, M., Journal of the American Chemical Society 1997, 119, 12710-12821

[Non-Patent Document 2] Gryaznov, S. M.; Letsinger, R. L., Journal of the American Chemical Society 1991, 113, 5876-5877

SUMMARY OF THE INVENTION

Problems to be Solved by the Invention

However, in the above H-phosphonate method, the occurrence of such a side reaction of the base moiety as intramolecular cyclization will be exponentially increased in the DNA synthesis as the length of a chain becomes longer. As a result, it will be very difficult to prepare a desired DNA oligomer as a main component after the synthesis has proceeded to give a 12-mer. Furthermore, DNA containing a cytosine residue would cause lots of the side reaction. There has been known no effective way to prevent said side reaction.

Means for Solving the Problems

The present inventors have tried to solve the above problems by forming an active phosphite intermediate in the phosphoramidite method wherein a long chain oligomer can be easily synthesized, leading to a new method for the synthesis of DNA using hydroxyl group-selective phosphorylation.

Thus, the present invention relates to a phosphoramidite method for the synthesis of a nucleic acid oligomer with the use of an alcohol-type activator, preferably of a mixture or combination of the alcohol-type activator and an acid catalyst.

Advantages of the Invention

Up to now, the 12-mer was the longest oligomer that could be synthesized in the conventional methods without protecting the base moiety. According to the present invention, however, it is now possible to synthesize a DNA oligomer consisting of a 10-mer or a longer one, such as, for example, that consisting of a 20-mer with an extremely high purity on a solid phase. The resulting DNA oligomers may be advantageously used for a DNA chip.

Best Mode for Carrying Out the Invention

The "alcohol-type activator (compound)" in this specification means a compound that makes it possible to form the active phosphite intermediate in the phosphoramidite method, but does not mean a compound wherein a hydrogen atom of an aliphatic hydrocarbon is replaced by a hydroxyl group. Any alcohol-type activator known to those skilled in the art may be used, being preferably selected from the group consisting of hydroxybenzotriazole-1-ol (HOBt), a HOBt-derivative and a phenol analogue in order to attain a high condensation efficiency (for example, 95% or more). The HOBt-derivative preferably has 1-4 substituents such as nitro-, bromo-, iodo-, and trifluoromethyl group, being, for example, 6-trifluoromethylbenzotriazole-1-ol, 6-nitrobenzotriazole-1-ol, or 4-nitro-6-trifluoromethyl benzotriazole-1-ol. It is more preferably that the HOBt-derivative has different substituents such as the trifluoromethyl and nitro groups at its 4 and/or 6 positions.

Any phenol analogue known to those skilled in the art may be used, being preferably 2,4-dinitrophenol, 3,4-dicyanophenol and 2-nitro-4-trifluoromethylphenol in order to attain the high condensation efficiency as well.

Any acid catalyst known to those skilled in the art may be used, being preferably imidazole, tetrazole and their derivatives such as, for example, benzimidazoletriflate (BIT), 4-ethylthiotetrazole, imidazolium triflate(trifluoromethane sulfonate) and 4,5-dicyanoimidazole.

A ratio of the compounds in the combination of the alcohol-type activator and the acid catalyst may be optionally selected by those skilled in the art depending on conditions such as the kinds of each compound and reaction solvent, being usually an equivalent ratio of 1:10-10:1.

The synthesis method of the present invention may be carried out in any system such as liquid or solid phase, being preferably carried out on a solid phase support for an industrial production of the oligomers. Any solid phase support known to those skilled in the art may be used, including CPG or HCP.

The nucleic acid according to the present invention may be DNA or RNA, which may comprise not only natural-occurring bases but also their various variants or analogues having cyclonucleoside structure in a sugar moiety or various substituents at their 2' and/or 4' positions. Their phosphoric acid moiety may have phosphorothionate or methylphosphonate structure.

Various reaction conditions in the phosphoramidite method, which are not specifically described in the present specification, may be optionally selected by those skilled in the art.

EXAMPLES

The present invention will be explained more in detail in line with the examples, which should not be construed to impose any limitations on the scope of the present invention.

Example 1

Solid Phase Synthesis of Dimer

Selectivity for the hydroxyl group (hydroxyl group-selectivity) in the present invention was examined by using HCP solid phase support having an end thymidine introduced thereon. Phosphorylation was carried out for one minute between 20 equivalents of amidite units comprising each base (A, C, G, T) and 40 equivalents of various activators for said end hydroxyl group on the HCP solid phase support, followed by oxidation with 0.1 M iodine solution (pyridine: water=9:1) for 2 min at a room temperature. A DMTr group was then removed with 3% trichloroacetic acid-$CH_2Cl_2$ solution for one minute at a room temperature, and a phosphoric acid-protecting group (2-cyanothyl group) was excised with ammonia for 12 hours at a room temperature.

When the conventional activator, IMT, was used, d[ApT] and d[CpT] were obtained with the hydroxyl group selectivity of 77% and 83%, respectively. On the other hand, when HOBt was used as the activator, d[ApT] and d[CpT] were obtained with the hydroxyl group selectivity of 99.7% 99.9%, respectively. The hydroxyl group-selectivity was calculated from a ratio of the area of peaks of the desired compound and N-phosphate.

Example 2

Solid Phase Synthesis of Trimer

Various trimers were synthesized in order to confirm utility of HOBt in the synthesis of DNA without protecting the base moiety. The dimmers were synthesized according to the method of Example 1 using HOBt as the activator, further followed by condensation to produce trimers. When IMT was used, the production of a considerable amount of side-products was observed in the synthesis of d[TpApT] and d[TpCpT]. The results are shown in TABLE 1. It also shows the results obtained by using NBT, an activator for a proton-block method, in $CH_3CN$—NMP mixture solvent system.

Example 3

Synthesis of a Long Chain-Oligomer Using a DNA Synthesizer d[CCCCCTTTTCTCTCTCTCT](SEQ ID NO:1) and [TTAAAAATTATTAAATTATT](SEQ ID NO:2) were synthesized by means of DNA/RNA Synthesizer 392 (Applied Biosystem Inc. (ABI)). The synthesis of the DNA oligomer was carried out using HCP solid phase support having an end thymidine introduced thereon (1 μmol, 28 μmol/g, succinyl linker) and a mixture of 0.2 M Ho$^{tf}$Bt (6-trifluoromethylbenzotriazole-1-ol: the alcohol-type activator) and 0.2 M BIT (benzimidazoletriflate: the acid catalyst) in $CH_3CN$—N-methyl-2-pyrrolidone (15:1, v/v) solvent. Each elongation cycle of the synthesis is shown in TABLE 2.

TABLE 2

| step | operation | reagent(s) | time, (min) |
|---|---|---|---|
| 1 | washing | $CH_3CN$ | 0.2 |
| 2 | detritylation | 3% $Cl_3CCOOH$ / $CH_2Cl_2$ | 1.5 |
| 3 | washing | $CH_3CN$ | 0.4 |
| 4 | coupling | 0.1 M amidite + 0.2 M HO$^{tf}$Bt + 0.2 M BIT in $CH_3CN$-NMP (15:1, v/v) | 1.0 |
| 5 | washing | $CH_3CN$ | 0.2 |
| 6 | coupling | 0.1 M amidite + 0.2 M HO$^{tf}$Bt + 0.2 M BIT in $CH_3CN$-NMP (15:1, v/v) | 1.0 |
| 7 | washing | $CH_3CN$ | 0.2 |
| 8 | oxidation | 0.1 M $I_2$ in Py-$H_2O$-THF (20:2:78, v/v/v) | 0.5 |
| 9 | washing | $CH_3CN$ | 0.4 |

TABLE 1

| | | | % ratio of the desired product | | | |
|---|---|---|---|---|---|---|
| compd | polymer | final product | IMT | NBT | HOBt | HO″Bt |
| 2-11a | T-HCP | ApT | 77.0% | 99.2% | 99.7% | 99.3% |
| 2-11c | T-HCP | CpT | 82.9% | 99.0% | 99.9% | 98.9% |
| 2-11g | T-HCP | GpT | >99.9% | >99.9% | >99.9% | >99.9% |
| 2-4 | d[ApT]-HCP | TpApT | 90.5% | >99.9% | >99.9% | 99.1% |
| 2-4 | d[CpT]-HCP | TpCpT | 9.7% | 99.8% | >99.9% | 98.7% |
| 2-4 | d[GpT]-HCP | TpGpT | >99.9% | >99.9% | >99.9% | >99.9% |

| | % ratio of the desired product | | |
|---|---|---|---|
| compd | HO″Bt | HO‴Bt | DNP |
| 2-11a | 98.8% | 96.1% | 97.1% |
| 2-11c | 99.8% | 92.4% | 99.5% |
| 2-11g | >99.9% | >99.9% | >99.9% |
| 2-4 | 97.5% | 96.7% | 99.6% |
| 2-4 | 97.2% | 64.7% | 99.4% |
| 2-4 | >99.9% | >99.9% | >99.9% |

The DMTr group was then removed with 3% trichloroacetic acid in $CH_2Cl_2$ (2 mL) for one minute, and the solid phase support was washed with $CH_2Cl_2$ (1 mL×3) and $CH_3CN$ (1 mL×3). Finally the solid phase support was treated with conc. ammonia water (500 μL) to be excised to give a desired product.

d[CCCCCTTTTCTCTCTCTCT](SEQ ID NO: 1), Mass (M+H) calcd 5868.23, found 5869.92; Enzyme Assay dC:T=1.00:0.99, isolated yield 79%.

[TTAAAAATTATTAAATTATT](SEQ ID NO: 2), Mass (M+Na) calcd 6130.31, found 6132.69; Enzyme Assay dA:T=1.00:0.94, isolated yield 31%.

INDUSTRIAL APPLICABILITY

A DNA fragment having such a length as 20-mer or so is needed for an Affimetrix-type DNA chip, which is widely used for gene diagnosis. The success of the synthesis of such long DNA without protecting the base moiety has therefore made a start for a high throughput preparation of the DNA chip with a high cost performance, making a great impact on biotechnology. The present invention is the first synthesis method that can attain a practical level without protecting the base moiety. It is expected that the nucleic acid oligomers synthesized according to the present invention will be utilized in gene diagnosis such as SNP analysis.

wherein the phosphoramidite is contacted with an activator, and the activator comprises both a) an alcohol-type compound selected from the group consisting of hydroxybenzotriazole-1-ol (HOBt), a mono-substituted or d-substituted HOBt and a di-substituted phenol and b) an acid catalyst selected from the group consisting of imidazole, tetrazole, benzimidazoletriflate (BIT), 4-ethylthiotetrazole, imidazolium triflate(trifluoromethane sulfonate) and 4,5-dicyanoimidazole.

2. The method according to claim 1, wherein the substituted HOBt has substituents at its 4 and/or 6 positions.

3. The method according to claim 2, wherein the substituted HOBt is 6-trifluoromethylbenzotriazole-1-ol, 6-nitrobenzotriazole-1-ol, or 4-nitro-6-trifluoromethyl benzotriazole-1-ol.

4. The method according to claim 1, wherein the di-substituted phenol is selected from the group consisting of 2,4-dinitrophenol, 3,4-dicyanophenol and 2-nitro-4-trifluoromethylphenol.

5. The method according to claim 1, wherein said activator comprises an equal amount of the alcohol-type compound and the acid catalyst.

What is claimed is:

1. A phosphoramidite method for the synthesis of a nucleic acid oligomer without protecting the base moiety, which comprises:

reacting a 3' or 5' hydroxyl group of a nucleotide, optionally attached to a solid phase support, with a nucleoside phosphoramidite, a cyclonucleoside phosphoramidite, a 2'-substituted nucleoside phosphoramidite, a 4'-substituted nucleoside phosphoramidite, or a 2',4'-di-substituted nucleoside phosphoramidite to produce a phosphodiester linkage;

6. The method according to claim 1, wherein said method is carried out with the nucleotide attached to a solid phase support.

7. The method according to claim 1, wherein the activator comprises 6-trifluoromethylbenzotriazole-1-ol and benzimidazoletriflate.

8. A phosphoramidite method for the synthesis of a nucleic acid oligomer without protecting the base moiety, which comprises:

reacting a 3' or 5' hydroxyl group of a nucleotide, optionally attached to a solid phase support, with a nucleoside phosphoramidite, a cyclonucleoside phosphoramidite, a 2'-substituted nucleoside phosphoramidite, a 4'-substituted nucleoside phosphoramidite, or a 2',4'-di-substituted nucleoside phosphoramidite to produce a phosphodiester linkage;

wherein the phosphoramidite is contacted with an activator, and the activator comprises a) an alcohol-type compound selected from the group consisting of hydroxybenzotriazole-1-ol (HOBt), 6-trifluoromethylbenzotriazole-1ol, 6-nitrobenzotriazole-1-ol, 4-nitro-6-trifluoromethyl benzotriazole-1-ol, 2,4-dinitrophenol, 3,4-dicyanophenol and 2-nitro-4-trifluoromethylphenol; and b) an acid catalyst selected from the group consisting of imidazole, tetrazole, benzimidazoletriflate (BIT), 4-ethylthiotetrazole, imidazolium triflate(trifluoromethane sulfonate) and 4,5-dicyanoimidazole.

* * * * *